(12) United States Patent
Hashimoto

(10) Patent No.: US 7,684,603 B2
(45) Date of Patent: Mar. 23, 2010

(54) COMPLETE FIELD OF VIEW OF CONTRAST MEDIUM IN A TIME-VARYING ULTRASONIC IMAGING APPARATUS

(75) Inventor: Hiroshi Hashimoto, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1048 days.

(21) Appl. No.: 11/238,785

(22) Filed: Sep. 29, 2005

(65) Prior Publication Data
US 2006/0067567 A1    Mar. 30, 2006

(30) Foreign Application Priority Data
Sep. 30, 2004 (JP) ............................. 2004-286186
Mar. 18, 2005 (JP) ............................. 2005-078570

(51) Int. Cl.
G06K 9/00 (2006.01)
A61M 5/00 (2006.01)

(52) U.S. Cl. ....................................... 382/131; 600/432

(58) Field of Classification Search ................. 382/131; 73/606, 620, 626, 629; 600/442, 443, 455, 600/432
See application file for complete search history.

(56) References Cited

U.S. PATENT DOCUMENTS

| 5,456,255 | A |   | 10/1995 | Abe et al. |         |
|-----------|---|---|---------|------------|---------|
| 5,833,613 | A | * | 11/1998 | Averkiou et al. | 600/440 |
| 5,840,034 | A |   | 11/1998 | Amemiya et al. |     |
| 6,146,330 | A |   | 11/2000 | Tujino et al. |      |
| 6,149,597 | A | * | 11/2000 | Kamiyama | 600/458 |
| 6,245,017 | B1 |  | 6/2001  | Hashimoto et al. |  |
| 6,245,019 | B1 |  | 6/2001  | Kamiyama |         |
| 6,374,674 | B1 |  | 4/2002  | Mine |             |
| 6,464,642 | B1 |  | 10/2002 | Kawagishi |        |
| 6,679,843 | B2 | * | 1/2004 | Ma et al. | 600/441 |
| 2002/0055681 | A1 | * | 5/2002 | Averkiou et al. | 600/458 |
| 2003/0105605 | A1 | * | 6/2003 | Degani et al. | 702/104 |
| 2003/0171668 | A1 | * | 9/2003 | Tsujino et al. | 600/407 |
| 2004/0034297 | A1 | * | 2/2004 | Darrow et al. | 600/407 |
| 2004/0127790 | A1 | * | 7/2004 | Lang et al. | 600/438 |

FOREIGN PATENT DOCUMENTS

| JP | 06014923   | 1/1994 |
| JP | 2002045360 | 2/2002 |
| JP | 2003164452 | 6/2003 |

* cited by examiner

*Primary Examiner*—Charles Kim
*Assistant Examiner*—Nirav G Patel
(74) *Attorney, Agent, or Firm*—Armstrong Teasdale LLP

(57) ABSTRACT

An ultrasonic imaging apparatus includes an image data production device for producing image data composed of a plurality of frame image data items acquired successively from the subject during a scan time, a continuous time field image data production device for producing continuous time field image data from the image data by adding up the plurality of frame image data items acquired successively during the scan time, a time-sequential change process image data production device for producing time-sequential change process image data, and a synthesis/output device for synthesizing an image represented by the continuous time field image data and each of the images represented by the time-sequential change process image data by superimposing the image represented by the continuous time field image data on each of the images represented by the time-sequential change process image data.

16 Claims, 13 Drawing Sheets

Image information

Infiltrated field image data

Image data

Projection image data

Time

COMPLETE FIELD OF VIEW OF CONTRAST MEDIUM IN A TIME-VARYING ULTRASONIC IMAGING APPARATUS

CROSS REFERENCE TO RELATED APPLICATIONS

This application claims the benefit of Japanese Application No. 2004-286186 filed Sep. 30, 2004 and Japanese Application No. 2005-078570 filed Mar. 18, 2005.

BACKGROUND OF THE INVENTION

The present invention relates to an ultrasonic imaging apparatus, an image processing apparatus, and a program for producing time-varying tomographic image data, especially, tomographic image data representing an image of a contrast medium injected into a subject.

In recent years, an ultrasonic imaging apparatus has been used to image a subject by injecting a contrast medium into the subject. The contrast medium is a liquid containing numerous microscopic bubbles. The liquid injected into a subject circulates through the subject's body with the passage of time. Ultrasonic waves emitted from the ultrasonic imaging apparatus become nonlinear due to the microscopic bubbles in a region through which the contrast medium has circulated, and are observed as echoes having a harmonic.

When a contrast medium is injected into a subject in order to produce image data using an ultrasonic imaging apparatus, part of the image data carried by a harmonic represents a field into which the contrast medium is infiltrated. A time-sequential change of fields indicates the progress of infiltration or circulation of the contrast medium into or through a subject. The progress serves as information important to specify various diseases.

Moreover, even when image data is acquired using a color flow mapping (CFM) technique that does not employ a contrast medium, an image of a field displayed in colors according to the image data shows time-sequential or spatial circulation of blood, and provides information that is important to specify various diseases.

[Non-Patent Document 1] "Guide to Ultrasonic Contrast Imaging" (Fuminori Moriyasu et al., Kanehara Publishing, Feb. 28, 2003, p. 54-55)

However, according to the background art, the positional relationship between a region in a subject, in which a contrast medium lies and which is being imaged, and any other region into which the contrast medium may be infiltrated is not clarified. Namely, an image displayed on an ultrasonic imaging apparatus renders only a field in which the contrast medium lies and which is being imaged. The other fields cannot be discerned because of a low signal strength.

In particular, all fields in a subject into which a contrast medium is infiltrated during a period from the instant an image is initially displayed to the instant the image disappears cannot be discerned simultaneously. Nevertheless, when an operator interprets an image, pieces of image information representing the images of all the fields into which the contrast medium is infiltrated are very important to specify a field into which the contrast medium is infiltrated and which is being visualized and to recognize a time-sequential change of such fields.

Moreover, even when image data is acquired from blood flow using the CFM technique, an image of a field displayed in colors according to the image data partly shows time-sequential or spatial circulation of blood. It is important for an operator to discern all fields through which blood circulates time-sequentially or spatially.

Consequently, what counts is how to realize an ultrasonic imaging apparatus, an image processing apparatus, and a program that help an operator recognize all fields in a subject, into which a contrast medium is infiltrated, concurrently with a visualized region of the subject in which the contrast medium lies.

SUMMARY OF THE INVENTION

Therefore, an object of the present invention is to provide an ultrasonic imaging apparatus, an image processing apparatus, and a program that help an operator recognize all fields in a subject, into which a contrast medium is infiltrated, concurrently with a visualized region of the subject in which the contrast medium lies.

In order to solve the foregoing problems and accomplish the object of the present invention, an ultrasonic imaging apparatus in accordance with the first aspect of the present invention comprises: an image data production means for scanning a subject with ultrasonic waves, receiving ultrasonic echoes from the subject, and producing image data composed of a plurality of frame image data items acquired successively from the subject during a scan time; a display means for displaying an image produced based on the image data; a storage means for preserving the image data; a continuous time field image data production means for producing continuous time field image data from the image data by adding up the plurality of frame image data items acquired successively during the scan time; a time-sequential change process image data production means for producing time-sequential change process image data, which represents a plurality of frame images showing a process that pixel values changes from one values to another with the passage of time during the scan time, from the image data; and a synthesis/output means for synthesizing an image represented by the continuous time field image data and each of the images represented by the time-sequential change process image data by superimposing the image represented by the continuous time field image data on each of the images represented by the time-sequential change process image data, and transmitting the resultant image to the display means by sequentially changing the images represented by the time-sequential change process image data with the passage of time during the scan time.

Moreover, according to the second aspect of the present invention, an ultrasonic imaging apparatus comprising: an image data production means for receiving ultrasonic echoes from a subject and producing image data composed of a plurality of frame image data items acquired successively from different fields within a region of imaging that are lined in the thickness direction of imaging sections; a display means for displaying an image produced based on the image data; a storage means for preserving the image data; a projection image data production means for producing projection image data from the image data by adding up the plurality of frame image data items acquired successively in the thickness direction; a field change process image data production means for producing field change process image data, which represents a plurality of frame images showing a process that pixel values change from one values to another along with the change of the fields within the region of imaging that are lined in the thickness direction, from the image data; and a synthesis/output means for synthesizing an image represented by the projection image data and each of the images represented by the field change process image data by superimposing the image represented by the projection image data on each of the images represented by the field change process image data, and transmitting the resultant image to the display means by sequentially changing the images represented by the field process image data along with the change of the fields within the region of imaging.

Moreover, according to the third aspect of the present invention, an ultrasonic imaging apparatus comprising: an image data production means for producing image data composed of a plurality of frame image data items, which represents a time-sequential change in the same visualized region, after a contrast medium is injected into a subject; a display means for displaying images represented by the pieces of image information; a storage means for preserving the pieces of image information; an infiltrated field image data production means for producing infiltrated field image data, which represents an image rendering all fields within the region into which the contrast medium is infiltrated, using the pieces of image information; an infiltration process image data production means for producing infiltration process image data, which represents a plurality of image frames showing a process of infiltration of the contrast medium into the region, using the pieces of image information; and a synthesis/output means for superimposing or synthesizing each of images represented by the infiltration process image data on or with an image represented by the infiltrated field image data, and transferring the resultant image to the display means while sequentially changing the images represented by the infiltration process image data according to the process.

Moreover, according to the fourth aspect of the present invention, the infiltration area image data production means included in the ultrasonic imaging apparatus in accordance with the third aspect includes an addition means for adding up the plurality of pieces of image information.

Moreover, according to the fifth aspect of the present invention, the infiltrated field image data production means and infiltration process image data production means included in the ultrasonic imaging apparatus in accordance with the third or fourth aspect include a subtraction means for subtracting reference image information, which is devoid of information on the contrast medium, from the pieces of image information.

According to the fifth aspect of the present invention, the infiltrated field image data production means and infiltration process image data production means use the subtraction means to subtract the reference image information, which is devoid of information on the contrast medium, from the pieces of image information so as to thus remove background image data.

Moreover, according to the sixth aspect of the present invention, the infiltration process image data employed in the ultrasonic imaging apparatus in accordance with any of the third to fifth aspects contains as pixel information pixel values that are contained in the pieces of image information and that reflect amounts of the contrast medium.

Moreover, according to the seventh aspect of the present invention, the infiltration process image data employed in the ultrasonic imaging apparatus in accordance with any of the third to fifth aspects contains as pixel information times which pixel values contained in the pieces of image information require to become maximum.

Moreover, according to the eighth aspect of the present invention, the infiltration process image data employed in the ultrasonic imaging apparatus in accordance with any of the third to fifth aspects contains as pixel information time instants at which pixel values contained in the pieces of image information start growing.

Moreover, according to the ninth aspect of the present invention, the ultrasonic imaging apparatus in accordance with any of the third to eighth aspects further comprises an input unit that, when the image information employed is three-dimensional image information, is used to enter the position of a section image information on which is transmitted to the infiltration area image data production means, infiltration process image data production means, and synthesis/output means.

According to the ninth aspect of the present invention, the ultrasonic imaging apparatus receives the position of a section, image information on which is transmitted, from the input unit so as to designate a section at any position in any direction.

Moreover, according to the tenth aspect of the present invention, the synthesis/output means included in the ultrasonic imaging apparatus in accordance with the ninth aspect sequentially changes the positions of a section, image information on which is transmitted, according to the process.

According to the tenth aspect of the present invention, the synthesis/output means sequentially changes the positions of a section, image information on which is transmitted, according to the process so as to time-sequentially transmit an image of a section located at an optimal position.

Moreover, according to the eleventh aspect of the present invention, the sequential change performed in the ultrasonic imaging apparatus in accordance with the tenth aspect is the rotation of a section.

Moreover, according to the twelfth aspect of the present invention, the synthesis/output means included in the ultrasonic imaging apparatus in accordance with any of the ninth to eleventh aspects includes a production means for producing two-dimensional image information on a section from projection information produced from the infiltration area image data and infiltration process image data.

Moreover, according to the thirteenth aspect of the present invention, the projection information employed in the ultrasonic imaging apparatus in accordance with the twelfth aspect represents sum totals of projection values, which are produced from the infiltration area image data and infiltration process image data, calculated in a direction orthogonal to the section.

According to the thirteenth aspect of the present invention, projection information is projection data produced from three-dimensional image information.

Moreover, according to the fourteenth aspect of the present invention, the projection information employed in the ultrasonic imaging apparatus in accordance with the twelfth aspect represents maximum value among the projection values, which are produced from the infiltration area image data and infiltration process image data, detected in a direction orthogonal to the section.

According to the fourteenth aspect of the present invention, the projection information is maximum intensity projection data (MIP data) produced from three-dimensional image information.

Moreover, according to the fifteenth aspect of the present invention, the synthesis/output means included in the ultrasonic imaging apparatus in accordance with any of the third to fourteenth aspects displays each of images, which are represented by the infiltration process image data and superimposed on an image represented by the infiltrated field image data, in a color different from a color in which the image represented by the infiltrated field image data is displayed.

Moreover, according to the sixteenth aspect of the present invention, the synthesis/output means included in the ultrasonic imaging apparatus in accordance with any of the third to fifteenth aspects includes a selection means for selecting whether each of infiltration process images is superimposed on an infiltrated field image.

Moreover, according to the seventeenth aspect of the present invention, an image processing apparatus comprising: an interface via which tomographic image data composed of a plurality of frame image data items acquired successively from a subject during a scan time during which the subject is scanned is received; a display means for displaying an image produced based on the tomographic image data; a storage means for preserving the tomographic image data; a continuous time field image data production means for producing continuous time field image data from the tomographic image data by adding up the plurality of frame image data items acquired successively during the scan time; a time-sequential change process image data production means for producing time-sequential change process image data, which represents a plurality of frame images showing a process that pixel values change from one values to another with the passage of time during the scan time, from the image data; and a synthesis/output means for synthesizing an image represented by the continuous time field image data and each of the images represented by the time-sequential change process image data by superimposing the image represented by the continuous time field image data on each of the images represented by the time-sequential change process image data, and transmitting the resultant image to the display means by sequentially changing the images represented by the time-sequential change process image data along with the passage of time during the scan time.

Moreover, according to the eighteenth aspect of the present invention, an image processing apparatus comprising: an interface via which tomographic image data composed of a plurality of tomographic frame image data items acquired successively from different fields within a region of imaging that are lined in the thickness direction of imaging sections is received; a display means for displaying an image produced based on the tomographic image data; a storage means for storing the tomographic image data; a projection image data production means for producing projection image data from the tomographic image data by adding up the plurality of tomographic frame image data items acquired successively in the thickness direction; a field change process image data production means for producing field change process image data, which represents a plurality of frame images showing a process that pixel values change from one to another along with the change of the fields within the region of imaging that are lined in the thickness direction, from the tomographic image data; and a synthesis/output means for synthesizing an image represented by the projection image data and each of the images represented by the field change process image data by superimposing the image represented by the projection image data on each of the images represented by the field process image data, and transmitting the resultant image to the display means by sequentially changing the images represented by the field change process image data along with the change of the fields within the region of imaging.

Moreover, according to the nineteenth aspect of the present invention, an image processing apparatus comprises: an interface via which a plurality of pieces of tomographic image information representing a time-sequential change in the same visualized region is received after a contrast medium is injected into a subject; a display means for displaying images represented by the pieces of tomographic image information; a storage means for preserving the pieces of tomographic image information; an infiltrated field image data production means for producing infiltrated field image data representing an image that renders all fields in the region into which the contrast medium is infiltrated and which are rendered in the tomographic images; an infiltration process image data production means for producing infiltration process image data that represents a plurality of image frames showing a process of infiltration of the contrast medium into the region; and a synthesis/output means for superimposing or synthesizing each of images represented by the infiltration process image data on or with an image represented by the infiltrated field image data, and transmitting the resultant image to the display means while sequentially changing the images represented by the infiltration process image data according to the process.

Moreover, according to the twentieth aspect of the present invention, the tomographic image information employed in the image processing apparatus in accordance with the nineteenth aspect is image data produced by an ultrasonic imaging apparatus.

Moreover according to the twenty-first aspect of the present invention, the infiltrated field image data production means included in the image processing apparatus in accordance with the nineteenth or twentieth aspect includes an addition means for adding up the plurality of pieces of tomographic image information.

Moreover, according to the twenty-second aspect of the present invention, the infiltration process image data employed in the image processing apparatus in accordance with any of the nineteenth to twenty-first aspects contains as pixel information pixel values that are represented by the pieces of image information and reflect amounts of the contrast medium.

According to the twenty-third aspect of the present invention, the synthesis/output means included in the image processing apparatus in accordance with any of the nineteenth to twenty-second aspects displays each of images, which is represented by the infiltration process image data and superimposed on an image represented by the infiltrated field image data, in a color different from a color in which the image represented by the infiltrated field image data is displayed.

According to the twenty-fourth aspect of the present invention, a program allowing a computer included in an image processing apparatus to function as: an interface via which tomographic image data composed of a plurality of frame image data items acquired successively from a subject during a scan time during which the subject is scanned is received; a display means for displaying an image produced based on the tomographic image data; a storage means for preserving the tomographic image data; a continuous time field image data production means for producing continuous time field image data from the tomographic image data by adding up the plurality of frame image data items acquired successively during the scan time; a time-sequential change process image data production means for producing time-sequential change process image data, which represents a plurality of frame images showing a process that pixel values change from one values to another along with the passage of time during the scan time, from the image data; and a synthesis/output means for synthesizing an image represented by the continuous time field image data and each of the images represented by the time-sequential change process image data by superimposing the image represented by the continuous time field image data on each of the images represented by the time-sequential change process image data, and transmitting the resultant image to the display means by sequentially changing the images represented by the time-sequential change process image data along with the passage of time during the scan time.

According to the twenty-fifth aspect of the present invention, a program allowing a computer included in an image processing apparatus to function as: an interface via which tomographic image data composed of a plurality of frame image data items acquired successively from different fields within a region of imaging that are lined in the thickness direction of imaging sections is received; a display means for displaying an image produced based on the tomographic image data; a storage means for preserving the tomographic image data; a projection image data production means for producing projection image data from the tomographic image data by adding up the plurality of tomographic frame image data items acquired successively in the thickness direction; a field change process image data production means for producing field change process image data, which represents a plurality of frame images showing a process that pixel values change from one values to another along with the change of the fields within the region of imaging that are lined in the thickness direction, from the tomographic image data; and a synthesis/output means for synthesizing an image represented by the projection image data and each of the images represented by the field change process image data by superimposing the image represented by the projection image data on each of the images represented by the field change process image data, and transmitting the resultant image to the display means by sequentially changing the images represented by the field change process image data along with the change of the fields within the region of imaging.

According to the twenty-sixth aspect of the present invention, a program allows a computer included in an image processing apparatus to function as: an interface via which a plurality of pieces of tomographic image information, which represents a time-sequential change in the same visualized region, is received after a contrast medium is injected into a subject; a display means for displaying images represented by the pieces of image information; a storage means for preserving the pieces of tomographic image information; an infiltrated field image data production means for producing infiltrated field image data, which represent an image rendering all fields in the region into which the contrast medium is infiltrated and which are rendered in the tomographic images, using the pieces of tomographic image information; an infiltration process image data production means for producing infiltration process image data, which represents a plurality of image frames showing a process of infiltration of the contrast medium into the region, using the pieces of tomographic image information; and a synthesis/output means for synthesizing or superimposing each of images represented by the infiltration process image data with or on an image represented by the infiltrated field image data, and transmitting the resultant image to the display means while sequentially changing the images represented by the infiltration process image data according to the process.

According to the present invention, after a contrast medium is injected into a subject, an image data production means produces image data composed of a plurality of frame image data items that render a time-sequential change in the same visualized region. A display means displays images produced based on the image data, and the storage means preserves the image data. Using the image data, an infiltrated field image data production means produces infiltrated field image data, which represents an image rendering all fields in the region into which the contrast medium is infiltrated. Using the image data, an infiltration process image data production means produces a plurality of pieces of infiltration process image data representing a process of infiltration of the contrast medium into the region. A synthesis/output means displays each of images represented by the infiltration process image data while superimposing the image on an image represented by the infiltrated field image data, and sequentially changes the images of the infiltration process image data according to the process of infiltration. Consequently, the process of infiltration of the contrast medium into the visualized region can be recognized in comparison with the whole of the fields into which the contrast medium is infiltrated. In particular, a time-sequential change or increase in the number of fields into which the contrast medium is infiltrated can be concretely sensed in comparison with the whole of the fields into which the contrast medium is infiltrated.

Further objects and advantages of the present invention will be apparent from the following description of the preferred embodiments of the invention as illustrated in the accompanying drawings.

DETAILED DESCRIPTION OF THE INVENTION

Referring to appended drawings, the best mode for realizing an ultrasonic imaging apparatus in accordance with the present invention will be described below. Noted is that the present invention will not be limited to the mode.

First Embodiment

Figure 1:
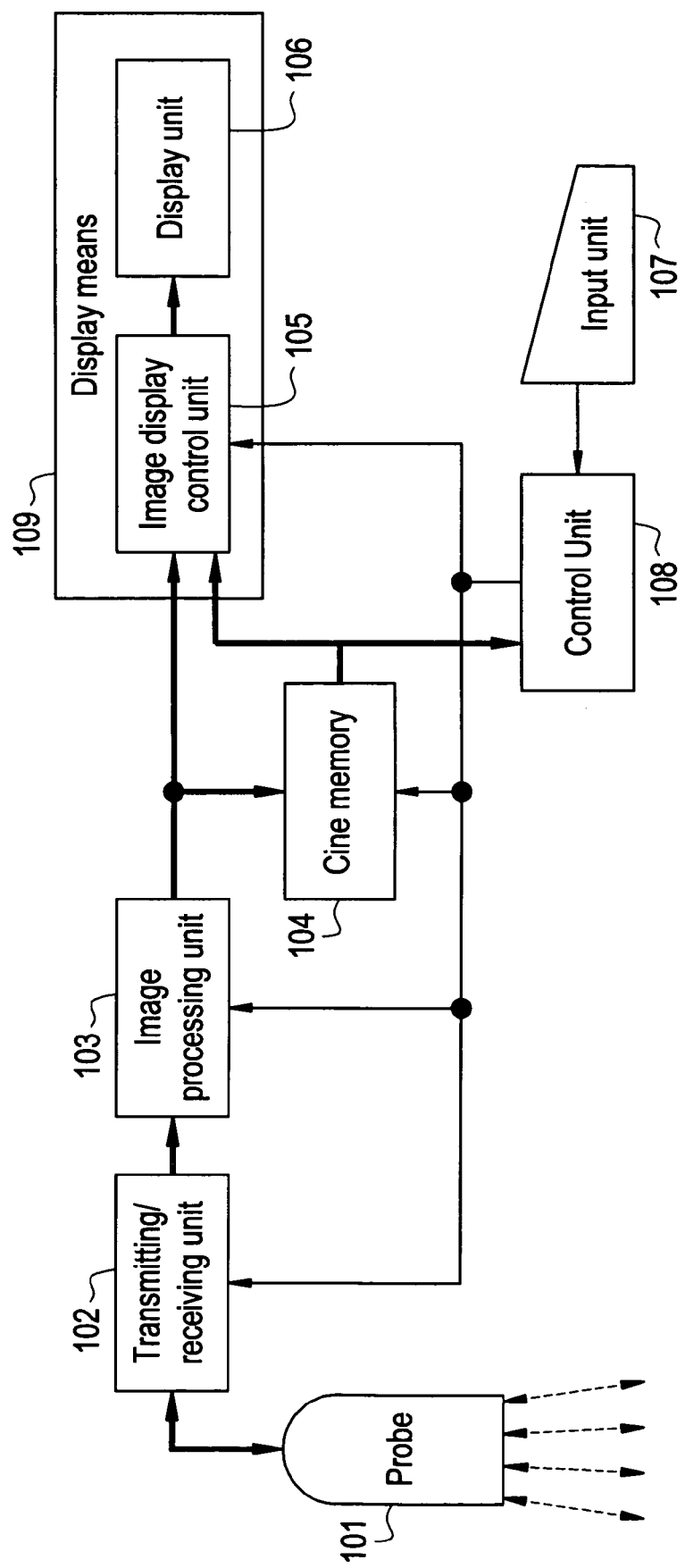
FIG. 1 is a block diagram showing the overall configuration of an ultrasonic imaging apparatus.

FIG. 1 is a block diagram showing the overall configuration of an ultrasonic imaging apparatus in accordance with an embodiment. The ultrasonic imaging apparatus comprises a probe 101, a transmitting/receiving unit 102, an image processing unit 103, a cine memory 104, an image display control unit 105, a display unit 106, an input unit 107, and a control unit 108. Incidentally, the probe 101, transmitting/receiving unit 102, image processing unit 103, and control unit 108 constitute an image data production means for producing image data which will be described later. The image display control unit 105 and display unit 106 constitute a display means 109. In FIG. 1, bolded lines linking the components express transmission lines over which analog or digital image data is transmitted, and thin lines express transmission lines over which control information is transmitted.

The probe 101 transmits or receives ultrasonic waves. Specifically, the probe 101 repeatedly irradiates ultrasonic waves in a specific direction on a section of a living body to be visualized, and receive echoes repeatedly reflected from the living body as time-sequential sound rays. Moreover, the probe 101 electronically scans the living body while sequentially changing irradiating directions of ultrasonic waves. The probe 101 has piezoelectric elements set in array, though the piezoelectric elements are not shown.

The transmitting/receiving unit 102 is connected to the probe 101 over a coaxial cable, and produces an electric signal with which the piezoelectric elements included in the probe 101 are driven. Moreover, the transmitting/receiving unit 102 initially amplifies received echoes.

The image processing unit 103 performs image processing so as to produce image data in real time using the echoes amplified by the transmitting/receiving unit 102. The concrete contents of the processing include, for example, summation of delays in received echoes, analog-to-digital (A/D) conversion, and writing of resultant digital information as image data in the cine memory 104 that will be described later. Incidentally, as the image data, data carried by a harmonic or a Doppler signal is adopted in order to render a contrast medium.

The Doppler signal is produced in Doppler mode by the image processing unit 103. In the Doppler mode, information on a phase shift which ultrasonic echoes undergo is sampled from the ultrasonic echoes amplified by the transmitting/receiving unit 102 in order to calculate in real time information on blood flow observed at points on an imaging section, such as, a velocity, a power, and a variance in velocity.

Moreover, the image processing unit 103 produces a CFM signal in CFM mode. In the CFM mode, information on blood flow carried by ultrasonic echoes is used to produce image data that represents an image of blood flow, which approaches the probe 101, in red and an image of blood flow, which recedes from the probe 101, in blue.

The cine memory 104 is a storage unit for storing or preserving image data resulting from image processing. In particular, image data that changes time-sequentially is preserved together with a time-sequential index that is used as basic data based on which the time-sequential change in image data is analyzed.

The image display control unit 105 converts a display frame rate, at which an image represented by image data produced by the image processing unit 103 is displayed, into another, and controls the shape of the image represented by image data or the position at which the image is displayed.

The display unit 106 uses a cathode-ray tube (CRT) or a liquid crystal display (LCD) to display an image, for which the display frame rate has been converted by the image display control unit 105 or whose shape or position have been controlled thereby, visibly to an operator.

The input unit 107 comprises a keyboard and a pointing device. An operator uses the input unit 107 to designate an action to be performed in the ultrasonic imaging apparatus or select image data representing an image to be displayed. Moreover, the input unit 107 serves as a selection means for use in selecting whether each of images represented by infiltration process image data should be superimposed on an image represented by infiltrated field image data.

The control unit 108 controls the actions of the components included in the ultrasonic imaging apparatus according to settings determined at the input unit 107 or selective information designated thereat, and a program and data stored in advance, and displays image data on the display unit 106.

Figure 2:
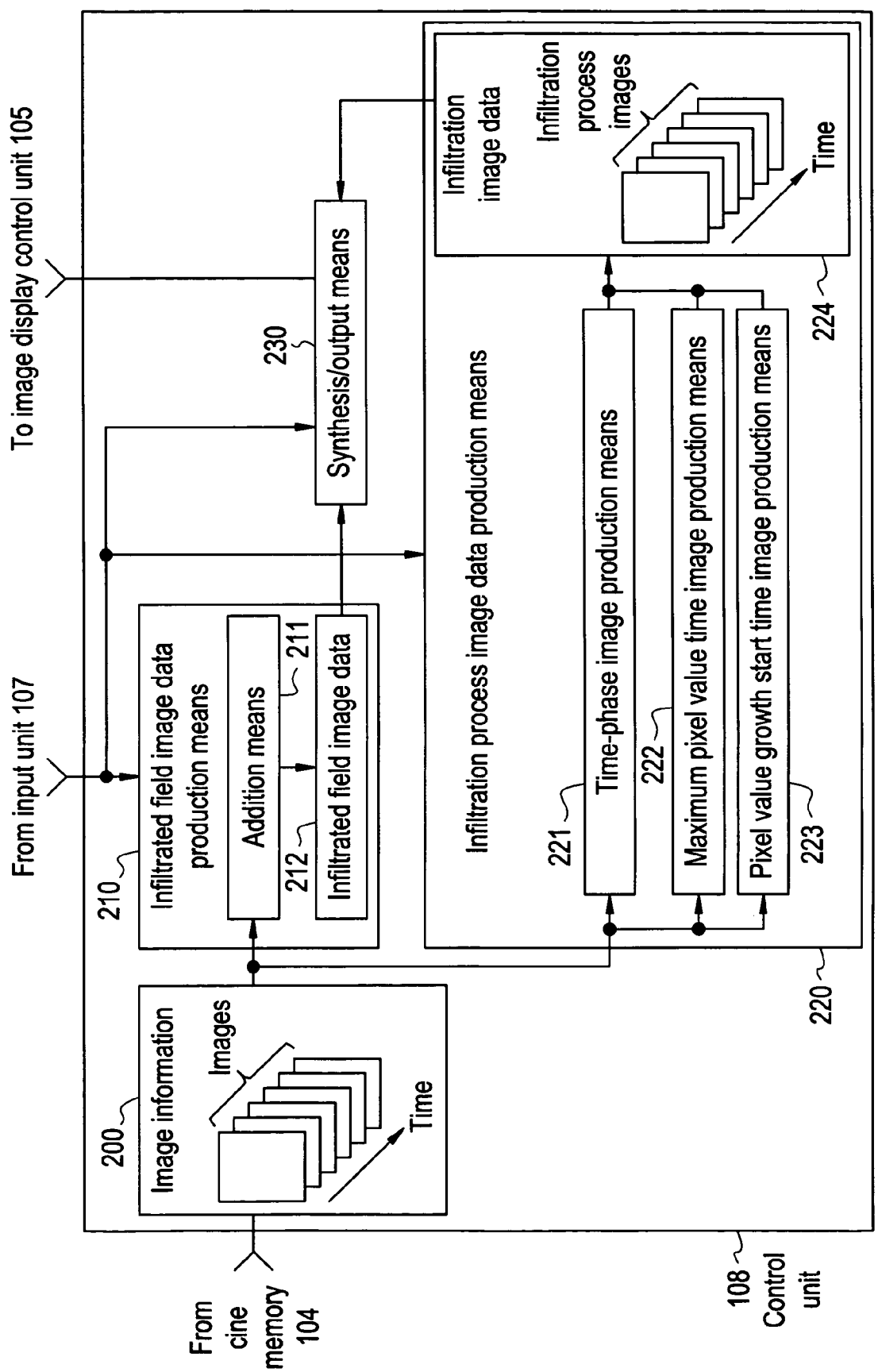
FIG. 2 is a functional block diagram showing the functional configuration of a control unit included in the first embodiment of the present invention.

FIG. 2 is a functional block diagram showing functional components of the control unit 108 in which the present invention is implemented. The control unit 108 comprises image data 200, an infiltrated field image data production means 210, an infiltration process image data production means 220, and a synthesis/output means 230. The image data 200 is transferred from the cine memory 104, and represents a plurality of images produced by time-sequentially acquiring echoes from the same visualized region of a subject. The image data 200 comprises time-sequential image data starting with data acquired at the time of injecting a contrast medium into a subject and ending with information acquired at the time of completing the infiltration of the contrast medium into the subject.

The infiltrated field image data production means 210 includes an addition means 211 for producing image data, which represents an image, by summating pixel values that are contained in a plurality of image data at the same location therein. The infiltrated field image data production means 210 uses the addition means 211 to produce filtrated field image data 212, which represents an image, from the image data 200.

The infiltration process image data production means 220 comprises a time-phase image production means 221, a maximum pixel value time image production means 222, and a pixel value growth start time image production means 223. The infiltration process image data production means 220 uses these pieces of image production means to produce infiltration process image data 224, which represents a process of infiltration of the contrast medium into a subject's body, from the image data 200. Incidentally, an operator uses the input unit 107 to select his/her desired image production means from among the time-phase image production means 221, maximum pixel value time image production means 222, and pixel value growth start time image production means 223. The selected image production means is used to produce an image.

The time-phase image production means 221 produces time-phase images that reflect amounts of a contrast medium in a visualized region which are in time-phase. Data items contained in the image data 200 are proportional to the amounts of the contrast medium that are in time-phase. Time-sequential images represented by the image data 200 are adopted as time-phase images as they are and the data on the time-phase images is regarded as the infiltration process image data 224.

The maximum pixel value time image production means 222 analyzes the plurality of time-sequential images represented by the image data 200 so as to measure a time from the start of measurement to the instant a pixel at the same location throughout the time-sequential images assumes a maximum value in relation to each of pixels contained in an image of the same visualized region. Pixels contained in images represented by pieces of image data acquired with the elapse of measured times are colored in order to produce infiltration process image data 224. The maximum pixel value time image data represents a time-sequential change of images rendering fields in which a maximum amount of the contrast medium is present.

The pixel value growth start time image production means 223 analyzes the plurality of time-sequential images represented by the image data 200 so as to measure a time from the start of the measurement to the instant the value of a pixel at the same location throughout the time-sequential images starts rising in relation to each of pixels that are contained in an image of a visualized region. Pixels contained in images represented by data acquired with the elapse of measured times are colored in order to produce infiltration process image data 224. The pixel value growth start time image information represents a time-sequential change of images rendering fields in which infiltration of the contrast medium is started.

The synthesis/output means 230 superimposes an image, which is represented by the infiltrated field image data 212, as a background image on each of images represented by the infiltration process image data 224. The resultant image is sequentially displayed on the display unit 106 along a time base used as an index for the images represented by the infiltration process image data 224. At this time, the image represented by the infiltrated field image data 212 to be superimposed on the images represented by the infiltration process image data 224 is colored in a color visually distinguishable from a color in which the images represented by the infiltration process image data 224 are displayed. For example, the image represented by the infiltrated field image data 212 is displayed as a monochrome image, and the images represented by the infiltration process image data 224 are displayed as color images of red or blue.

The superimposition is expressed as follows:

$$Disp_i = (1)$$

Herein, i denotes a frame number indicating image data that represents one of images lined along the time base used as an index for the images represented by the infiltration process image data 224. Disp denotes a value of a pixel included in an image displayed as a result of superimposition. F denotes a value of a pixel included in any of the images represented by the infiltration process image data 224. Therefore, $\Sigma F_i$ denotes the infiltrated field image data 212 representing the background image. Moreover, a and b denote weight coefficients that are used for superimposition and that also serve as indices expressing display forms, for example, colors.

As for the superimposition, the image display control unit 105 may be used to display both the images at the same position on the display unit 106. Alternatively, image data representing an image produced through superimposition may be produced separately and the image may then be displayed on the display unit 106.

Figure 3:
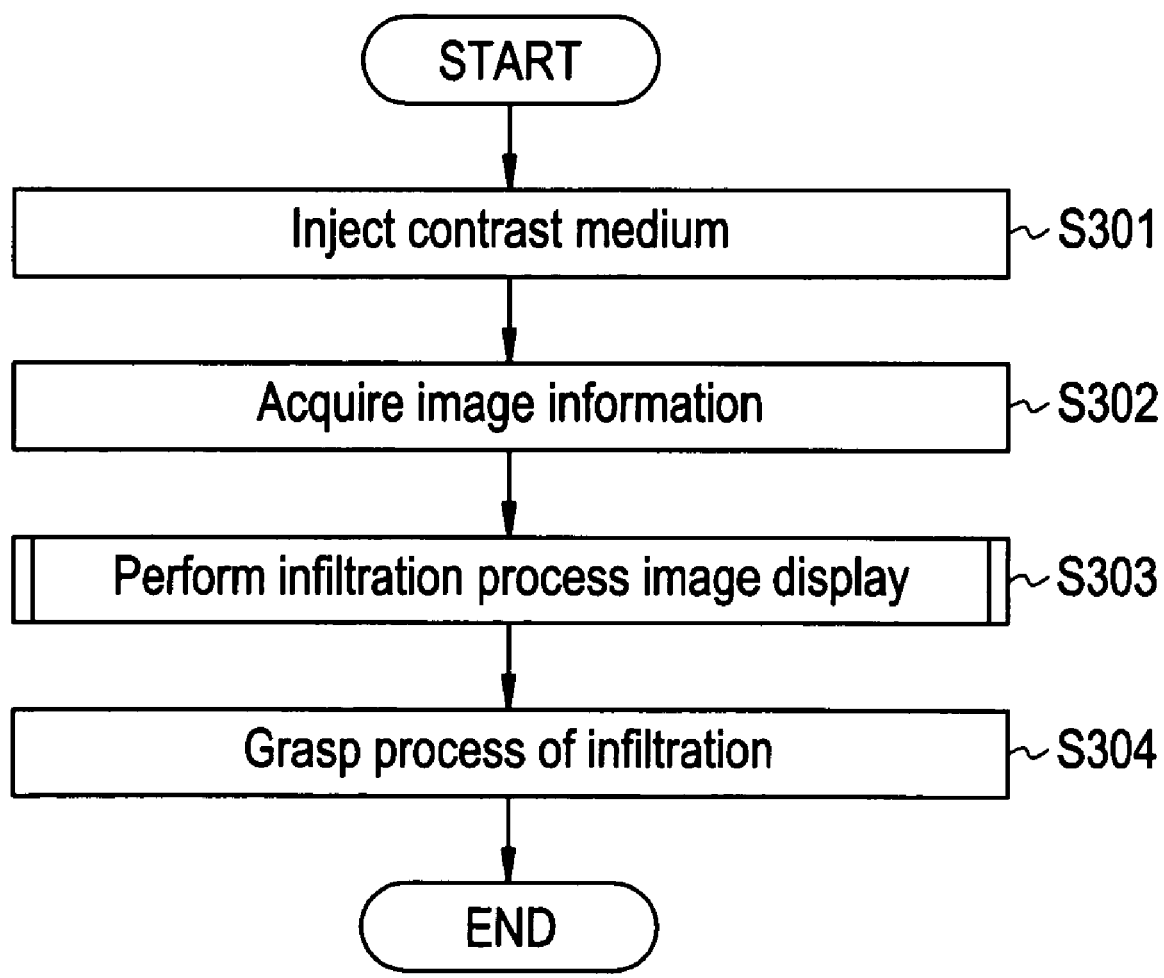
FIG. 3 is a flowchart describing actions to be performed in the ultrasonic imaging apparatus in accordance with the first embodiment of the present invention.
Figure 5:
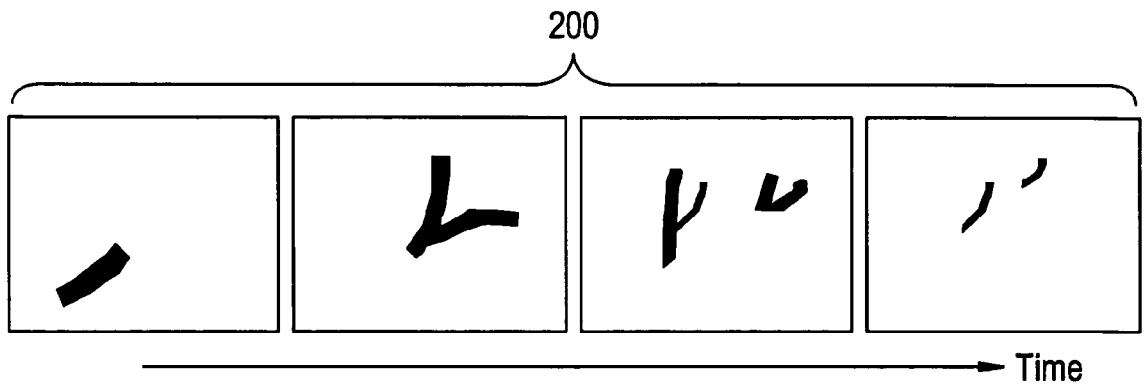
FIG. 5 is an explanatory diagram showing an example of images produced by the first embodiment of the present invention.

Referring to FIG. 3, actions to be performed in the ultrasonic imaging apparatus in accordance with the present invention will be described below. FIG. 3 is a flowchart describing the actions to be performed in the ultrasonic imaging apparatus. To begin with, an operator injects a contrast medium into a subject (step S301). The operator then brings the probe 101 into contact with an intended region of a subject, and acquires information on infiltration of the contrast medium into the subject as image data 200 (step S302). FIG. 5 shows an example of the acquired image data 200. The image data 200 represents a plurality of time-sequential images. Each of the images renders a field in the region of the subject into which the contrast medium is infiltrated. Since the images fragmentarily render only the fields in region into which the contrast medium is infiltrated, it is hard to accurately grasp one field, into which the contrast medium is infiltrated, in comparison with the other fields.

Thereafter, the ultrasonic imaging apparatus performs infiltration process image display (step S303). Namely, infiltration process images showing a process of infiltration of the contrast medium are displayed. The operator grasps the process of the infiltration of the contrast medium from the infiltration process images (step S304), and then terminates processing.

Figure 4:
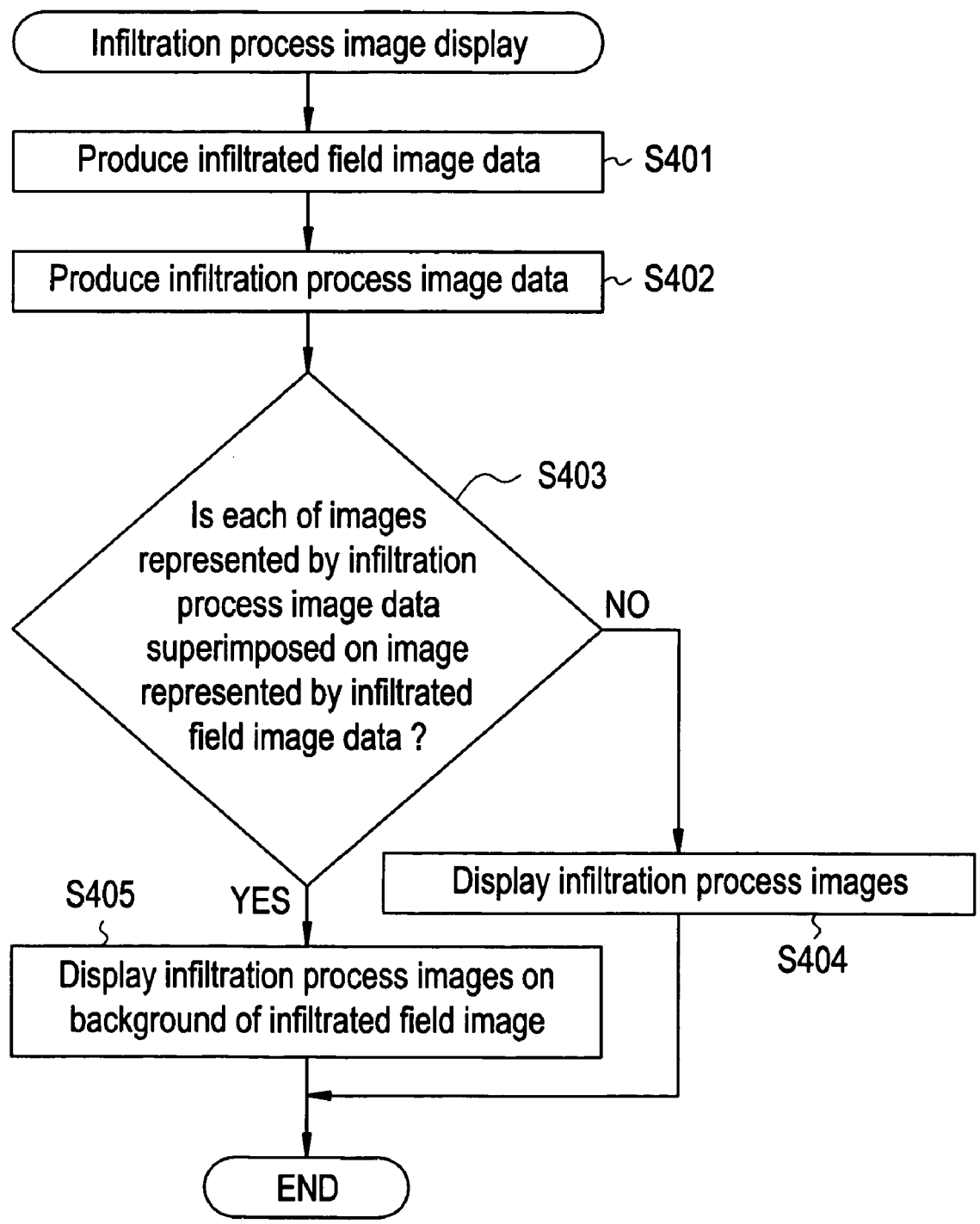
FIG. 4 is a flowchart describing infiltration process image display to be performed in the first embodiment of the present invention.
Figure 6:
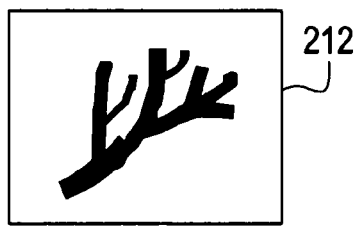
FIG. 6 is an explanatory diagram showing an example of an infiltrated field image produced by the first embodiment of the present invention.

Next, referring to FIG. 4, infiltration process image display of step S303 will be described below. FIG. 4 is a flowchart describing the infiltration process image display. First, the control unit 108 instructs the infiltrated field image data production means 210 to produce infiltrated field image data 212 from the image data 200 acquired at step S302 (step S401). FIG. 6 shows an example of an image represented by the infiltrated field image data 212 produced from the image data 200 that represents the images shown in FIG. 5. Images rendering fields in which the contrast medium is present at different time instants and which are fragmentarily rendered in the images shown in FIG. 5 are synthesized into one image. The image represented by the infiltrated field image data 212 includes all the images of the fields in which the contrast medium is present during a period from the instant the contrast medium is injected into the subject to the instant the infiltration of the contrast medium into the subject is completed.

Thereafter, the control unit 108 instructs the infiltration process image data production means 220 to produce infiltration process image data 224 (step S402). Based on instruction information entered at the input unit 107, the control unit 108 selects any of the time-phase image production means 221, maximum pixel value time image production means 222, and pixel value growth start time image production means 223 so as to produce the infiltration process image data 224. When the time-phase image production means 221 is selected, the image data 200 is adopted as the infiltration process image data 224 as it is, because the images represented by the image data 200 and shown in FIG. 5 are time-phase images showing a time-sequential change in the amount of the contrast medium.

Thereafter, based on instruction information entered at the input unit 107, the control unit 108 verifies whether each of images represented by the infiltration process image data 224 is superimposed on an image that is represented by the infiltrated field image data 212 and that serves as a background image (step S403). If each of the images represented by the infiltration process image data 224 is not superimposed on the image represented by the infiltrated field image data 212 (verified in the negative at step S403), the synthesis/output means 230 sequentially displays on the display unit 106 only the images represented by the infiltration process image data 224 (step S404).

Figure 7:
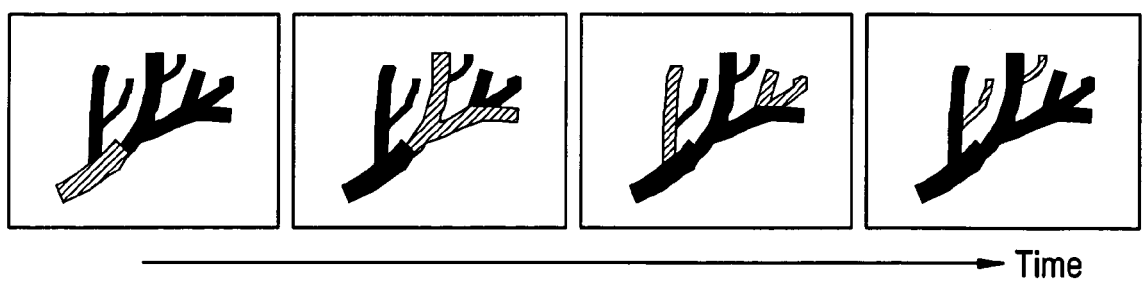
FIG. 7 is an explanatory diagram showing an example of infiltration process images superimposed on the infiltrated field image according to the first embodiment of the present invention.

Moreover, if each of the images represented by the infiltration process image data 224 is superimposed on the image represented by the infiltrated field image data 212 (verified in the affirmative at step S403), the control unit 108 instructs the synthesis/output means 230 to time-sequentially display on the display unit 106 each of the images represented by the infiltration process image data 224 on the background of the image represented by the infiltrated field image data 212 (step S405). FIG. 7 shows a time-sequential change, which is shown by the images represented by the infiltration process image data 224 and displayed on the background of the image represented by the infiltrated field image data 212, along the axis of abscissas that is a time base. Incidentally, the infiltration process image data 224 is produced by the time-phase image production means 221 that produces the images shown in FIG. 5.

In FIG. 7, the image represented by the infiltrated field image data 212 and shown in FIG. 6 is contained as a background image in all time-phase images. The time-phase images represented by the infiltration process image data 224 and shown in FIG. 5 are displayed as images of fields, which are indicated with hatched areas in FIG. 7, while being superimposed on the background image. The hatched areas in FIG. 7 indicate the images represented by the infiltration process image data 224. On the display unit 106, the images represented by the infiltration process image data 224 may be painted in a different color, for example, red.

As described above, according to the first embodiment of the present invention, the infiltrated field image data production means 210 produces the infiltrated field image data 212, which represents an image rendering all fields into which a contrast medium is infiltrated, using the image data 200 that represents a process of a time-sequentially change in infiltration of the contrast medium in a subject. The infiltration process image data production means 220 produces the infiltration process image data 224 that time-sequentially represents the process of infiltration. The synthesis/output means 230 superimposes each of the images represented by the infiltration process image data on the image represented by the infiltrated field image data and sequentially transfers the resultant image to the display means 109. Consequently, the process of infiltration of the contrast medium into a visualized region can be recognized in comparison with the whole of the fields into which the contrast medium is infiltrated. In particular, a time-sequential change or increase in the number of fields into which the contrast medium is infiltrated can be sensed concretely through comparison with the whole of the fields into which the contrast medium is infiltrated.

According to the first embodiment of the present invention, the control unit 108 included in the ultrasonic imaging apparatus uses the infiltrated field image data production means 210, infiltration process image data production means 220, or synthesis/output means 230 to perform infiltration process image display. An image processing apparatus separately connected to the ultrasonic imaging apparatus via an interface may be used to perform the same processing. In this case, the loads imposed on hardware of the ultrasonic imaging apparatus and on software thereof are lightened. When the image processing apparatus is used to perform infiltration process image display, information employed is not limited to image information but tomographic image information acquired using an X-ray CT system or a magnetic resonance imaging system will do.

Figure 8:
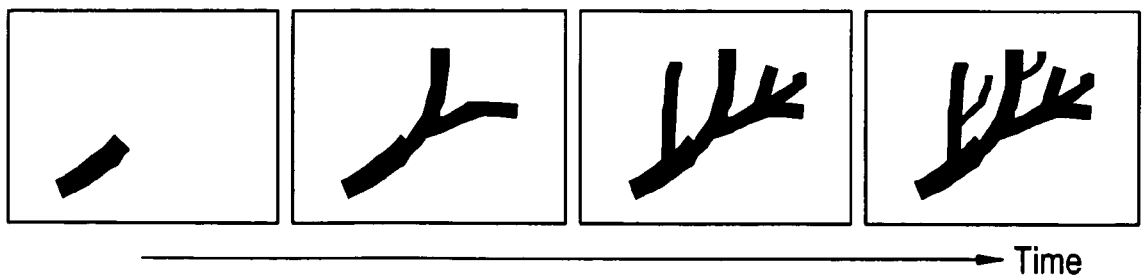
FIG. 8 is an explanatory diagram showing an example of images produced by performing capturing in an ultrasonic imaging apparatus.

According to the first embodiment of the present invention, the addition means 211 included in the infiltrated field image data production means 210 produces the infiltrated field image data 212. Alternatively, a so-called capture means that is a kind of addition means may be used to produce the infiltrated field image data 212. The capture means sequentially summates time-sequentially changing portions of images, which are represented by tomographic image information, and displays one resultant image that also indicates the process of a change. Image information fully handled by the capture means is identical to the infiltrated field image data 212. FIG. 8 shows an example of the image produced by the capture means using the image data 200 shown in FIG. 5. In FIG. 8, unlike FIG. 7, the image represented by the infiltrated field image data 212 is gradually completed with the passage of time. When the capture means is employed, it is hard to grasp the whole of fields, into which a contrast medium is infiltrated, at the beginning of capturing.

According to the first embodiment of the present invention, the image data 200 includes only image data produced from a region in which a contrast medium is present. Alternatively, the image data 200 may include background image data produced from a region in which the contrast medium is absent. In this case, the infiltrated field image data production means 210 and infiltration process image data production means are provided with a subtraction means that is not shown. The background image information representing a reference image that renders the region in which the contrast medium is absent is subtracted from the image data 200 in order to produce image information devoid of the background image information.

Moreover, according to the present first invention, the image data 200 includes pieces of two-dimensional tomographic image data representing planar images. Alternatively, the image data 200 may include three-dimensional tomographic image data rendering stereoscopic images. Moreover, the infiltrated field image data 212 and infiltration process image data 224 produced from the image data 200 may be three-dimensional image data items. In this case, when the image data items are handled by the synthesis/output means 230 and then transferred, the input unit 107 is used to arbitrarily designate the position of a section, on which two-dimensional image information is to be produced from the three-dimensional image information, and the direction thereof. Based on the data on the section, a production means that is not shown and included in the synthesis/output means 230 produces the two-dimensional image information.

Moreover, the production means produces two-dimensional image data from three-dimensional image data acquired by projecting an object included in a section. At this time, maximum intensity projection or the like may be employed. Namely, projection data that contains pixel values calculated as sum totals of pixel values contained in an image that is represented by the three-dimensional image data and that is to be projected, or maximum values of the pixel values contained in the image represented by the three-dimensional image data and to be projected are adopted as pixel values constituting a new image.

Moreover, the synthesis/output means 230 sequentially transmits two-dimensional image data produced from three-dimensional image data. At this time, the position of a section on which two-dimensional image information is produced may be changed by rotating the section. Consequently, a time-sequential change in a contrast medium can be traced using an image of a section located at an optimal position.

Second Embodiment

According to the first embodiment, a process that a contrast medium injected into a subject is infiltrated into the same region of imaging in the subject along with the passage of time is clearly discerned with an infiltrated field image, which shows all fields into which the contrast medium is infiltrated, as a background image. The probe 101 may be manually swept over a subject in a thickness direction orthogonal to imaging sections. Image data items acquired from a plurality of fields, that is, imaging sections and produced to represent an image of blood flow by performing color flow mapping (CFM) or the like may be used to clearly discern an image of each of the imaging sections or fields with a projection image of all the imaging sections as a background image. According to the second embodiment, an image of each imaging section or field is clearly discerned using a projection image.

Figure 9:
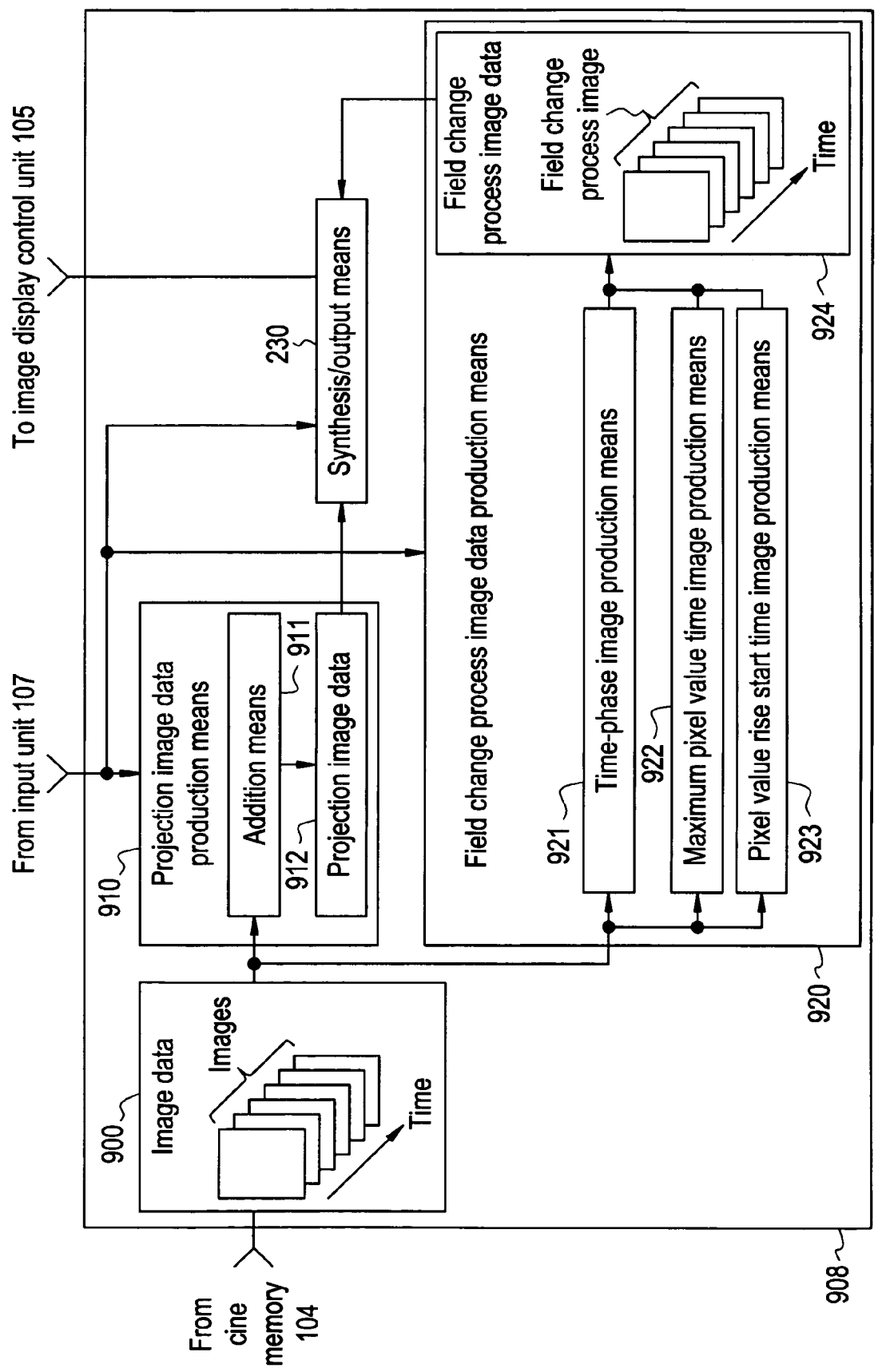
FIG. 9 is a functional block diagram showing the functional configuration of a control unit included in the second embodiment of the present invention.

The second embodiment of the present invention has the same hardware configuration as the first embodiment shown in FIG. 1 except the control unit 108. The description of the components other than the control unit 108 will therefore be omitted. FIG. 9 is a functional block diagram showing functional components of a control unit 908 included in the second embodiment. The control unit 908 is equivalent to the control unit 108 shown in FIG. 1.

The control unit 908 comprises image data 900, a projection image data production means 910, a field change process image data production means 920, and a synthesis/output means 230. The image data 900 is received from the cine memory 104. When the probe 101 is manually swept over a subject in a thickness direction orthogonal to an imaging section, a plurality of image data items is produced time-sequentially in synchronization with the sweep. The image data 900 refers to the plurality of image data items.

The projection image data production means 910 includes an addition means 911 that produces image data representing one image by adding up pixel values located at the same pixel location in the plurality of image data items. The addition means 911 produces projection image data, which has the plurality of image data items added up in a thickness direction, as projection image data 912 representing one image.

The field change process image data production means 920 includes a time-phase image production means 921, a maximum pixel value time image production means 922, and a pixel value rise start time image production means 923. The field change process image data production means 920 uses the image production means to produce field change process image data 924, which represents a process that fields in the same region of imaging in a subject are changed synchronously with sweep, on the basis of the image data 900. At the input unit 107, an image production means an operator wants to employ is selected from among the time-phase image production means 921, maximum pixel value time image production means 922, and pixel value rise start time image production means 923.

The time-phase image production means 921 produces a time-phase image that reflects pixels constituting an image of a region of imaging at each time phase during sweep. Incidentally, the image data 900 comprises pixel values acquired at time phases. Time-sequential images represented by the image data 900 are adopted as time-phase images as they are. The time-phase image data shall be called field change process image data 924.

The maximum pixel value time image production means 922 uses a plurality of time-sequential images represented by the image data 900 to detect a time elapsing from a start of measurement until a pixel value at each pixel location becomes maximum. The maximum pixel value time image production means 922 then produces field change process image data 924 representing in colors some of the pixels represented by the image data which is produced during the time. The maximum pixel value time image data indicates a time-sequential change of fields whose images are each represented by maximum pixel values.

The pixel value rise start time image production means 923 uses a plurality of time-sequential images represented by the image data 900 to detect a time elapsing from a start of measurement until a pixel value at each pixel location starts rising. The pixel value rise start time image production means 923 then produces field change process image data 924 representing in colors some of the pixels represented by the image data which is produced during the time. The pixel value rise start time image data indicates a time-sequential change of fields whose images are each represented by pixel values that have started rising.

The synthesis/output means 230 superimposes the image represented by the projection image data 912 as a background image data on each of images represented by the field change process image data 924, and sequentially displays the resultant image on the display unit 106 along a time base used as an index for the images represented by the field change process image data 924. At this time, the image represented by the projection image data 912 and the images represented by the field change process image data 924 that are superimposed on each other are colored to be visually discriminated from each other. For example, the image represented by the projection image data 912 is displayed as a monochrome image, and the images represented by the field change process image data 924 are displayed as color images of red or blue. The superimposition may be achieved using the image display control unit 105 so that the images to be superimposed on each other will be displayed at the same position on the display unit 106 or an image will be separately produced by superimposing images represented by different image data items on each other and then displayed on the display unit 106. The superimposition is expressed by the same formula as the formula (1).

Figure 10:
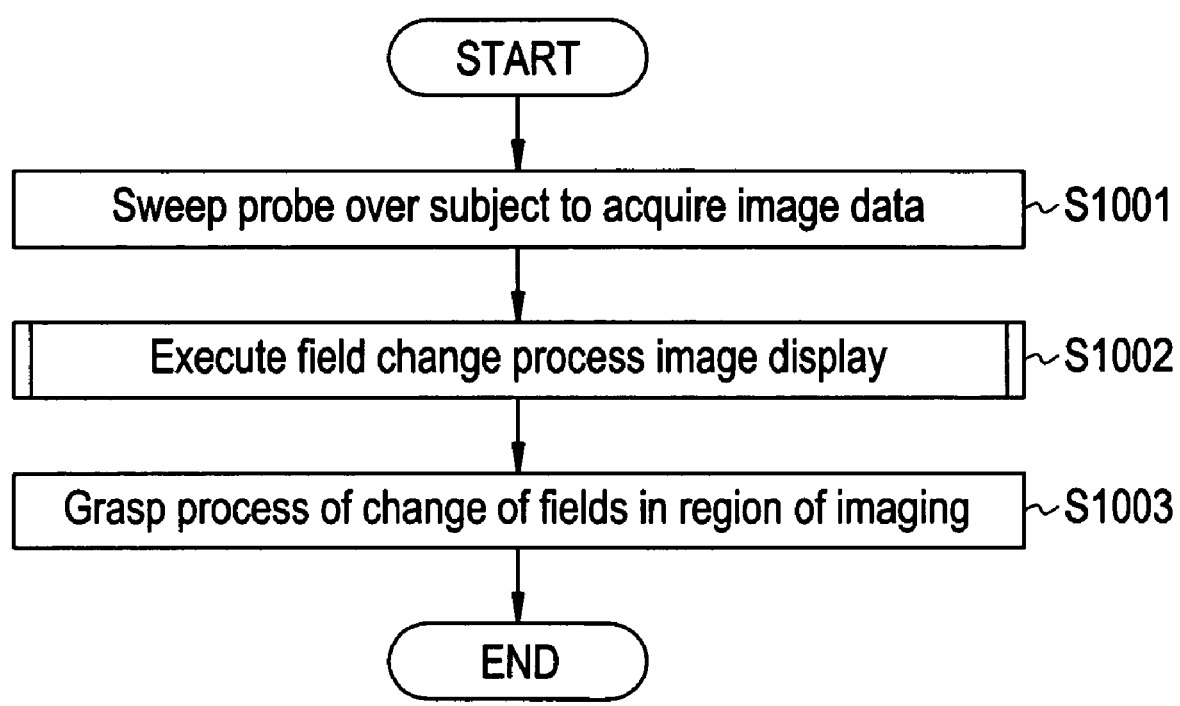
FIG. 10 is a flowchart describing actions to be performed in an ultrasonic imaging apparatus in accordance with the second embodiment.
Figure 12A:
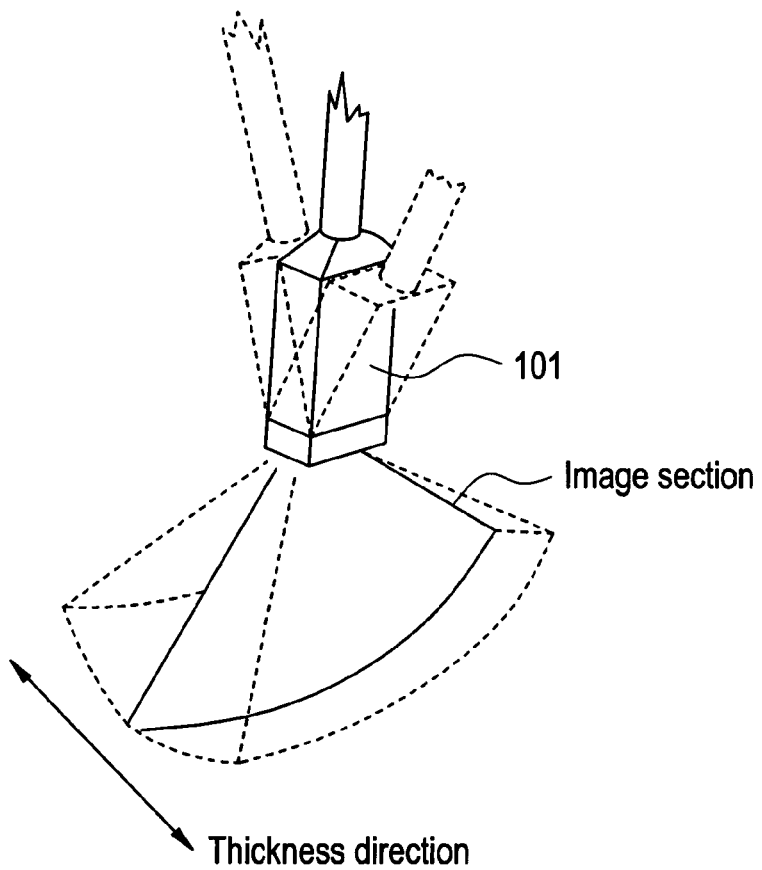
FIG. 12 is an explanatory diagram showing sweep of a probe included in the second embodiment.
Figure 12B:
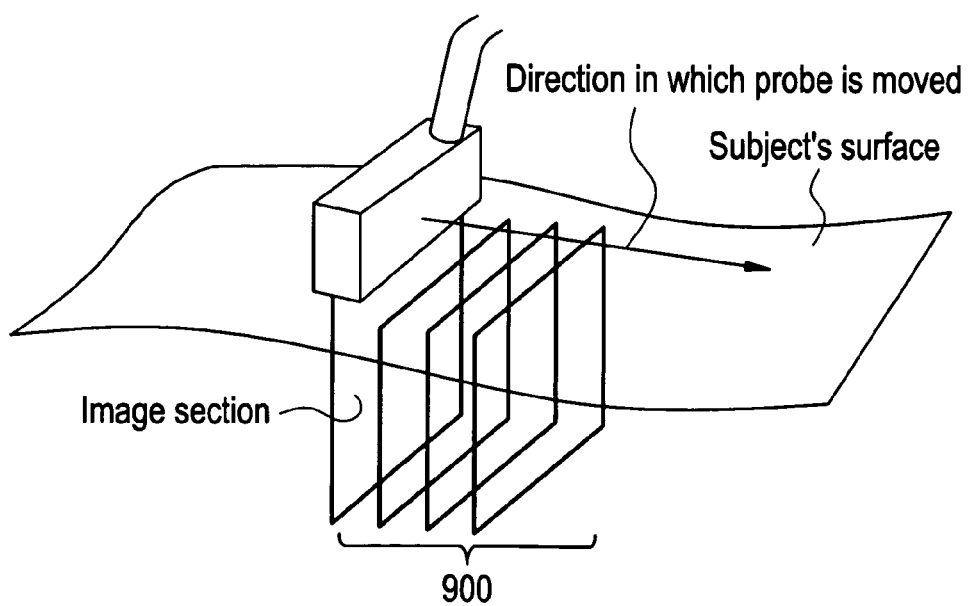

Next, actions to be performed by an ultrasonic imaging apparatus in accordance with the second embodiment will be described in conjunction with FIG. 10. FIG. 10 is a flowchart describing the actions to be performed by the ultrasonic imaging apparatus. To begin with, an operator manually sweeps the probe 101 over a subject, and a plurality of image data items is produced synchronously with the sweep (step S1001). FIG. 12(A) shows a case where the sector probe 101 is swept over a subject in a thickness direction substantially orthogonal to imaging sections. An operator brings the probe 101 into contact with an intended region on a subject, and manually sweeps it over the subject in a thickness direction orthogonal to imaging sections that are electronically scanned. In the case shown in FIG. 12(A), the region on which the probe 101 is put is substantially fixed, and the opening of the probe 101 through which ultrasonic waves are irradiated or ultrasonic echoes are received is swept in order to shift an irradiating direction in which ultrasonic waves are irradiated. The irradiating direction in which ultrasonic waves are irradiated through the opening of the probe 101 may be fixed, and the probe may be swept over a subject's region, on which the probe 101 is put, in the thickness direction. FIG. 12(B) shows a case where a linear probe is adopted, a direction in which ultrasonic waves are irradiated is fixed, and the probe is swept over a subject in a thickness direction. In this case, a plurality of image data items representing images of fields successively lined in the thickness direction orthogonal to imaging sections is produced. An operator produces as the image data 900 stereoscopic image data representing an image of the intended region of the subject.

Figure 13:
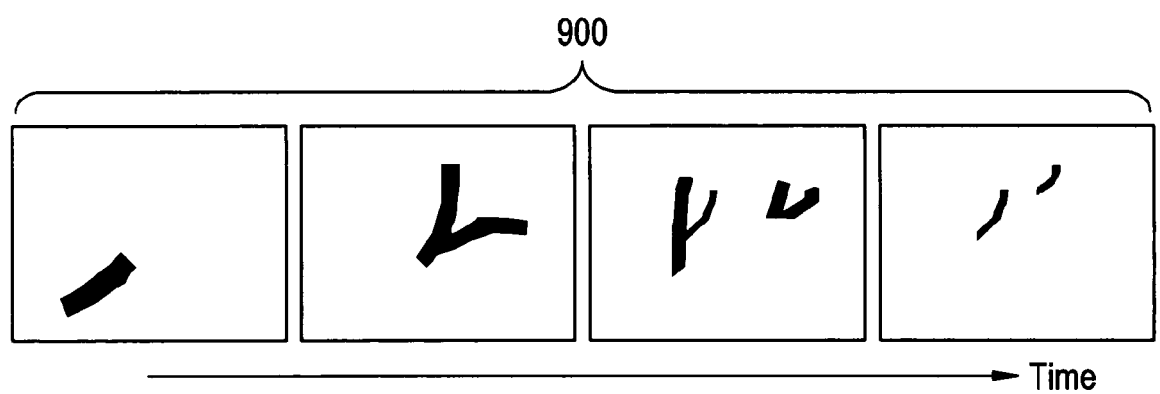
FIG. 13 is an explanatory diagram showing an example of images produced in the second embodiment.

FIG. 13 shows an example of the image data 900 produced in the CFM or Doppler mode. The image data 900 comprises a plurality of time-sequential image data items produced synchronously with sweep, and represents images of different fields lined in a thickness direction. Each of the images fractionally shows a field in which blood flow is present at the time of imaging. There is difficulty in accurately grasping all the fields in a region in which blood flow is present.

Thereafter, the ultrasonic imaging apparatus executes field change process image display (step S 1002), and displays field change process images showing a process of change of fields in which blood flow is present. An operator analyzes the field change process images so as to grasp the process of change of fields (step S1003). The processing is then terminated.

Figure 11:
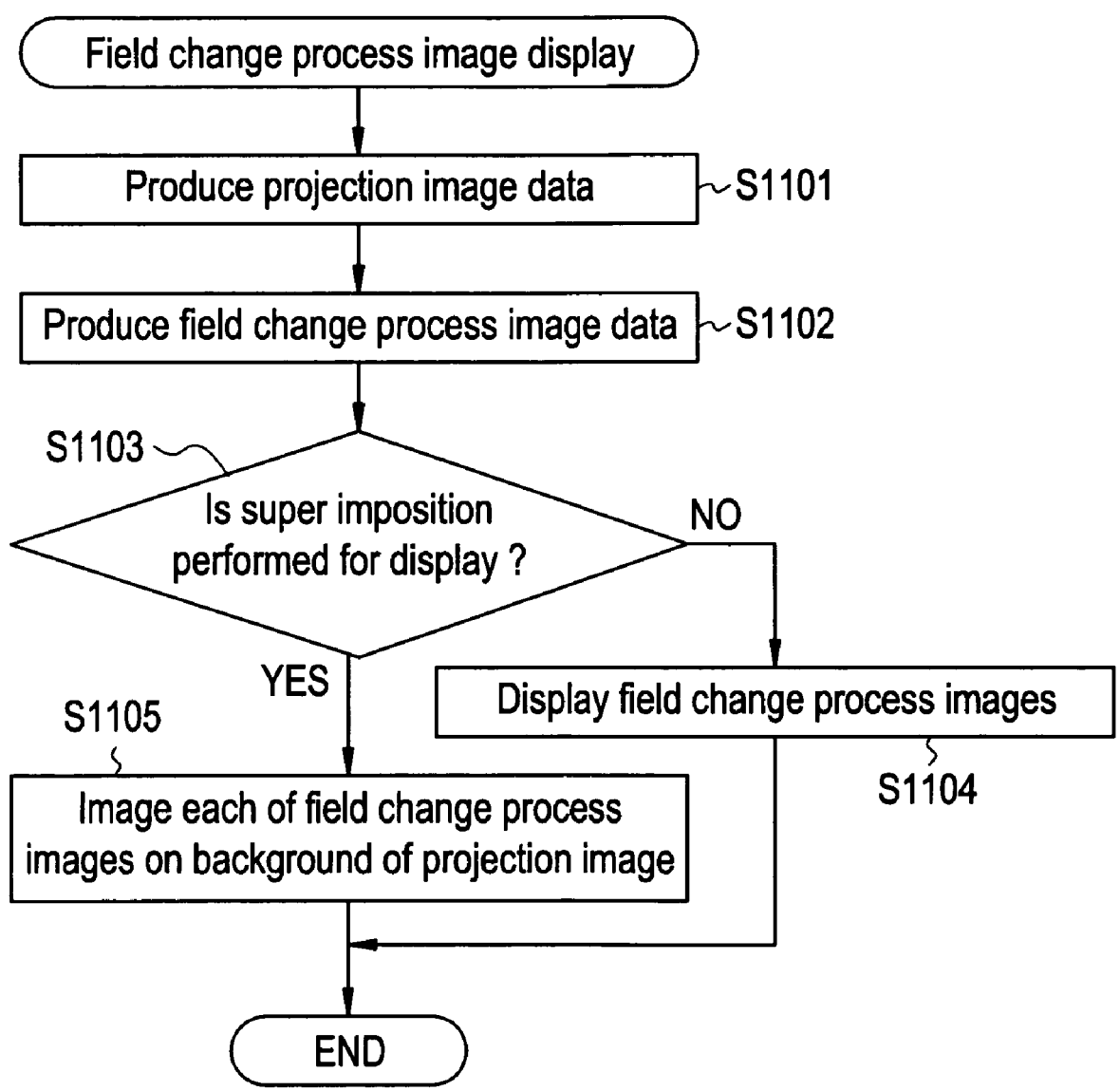
FIG. 11 is a flowchart describing actions to be performed during field change process image display in the second embodiment.
Figure 14:
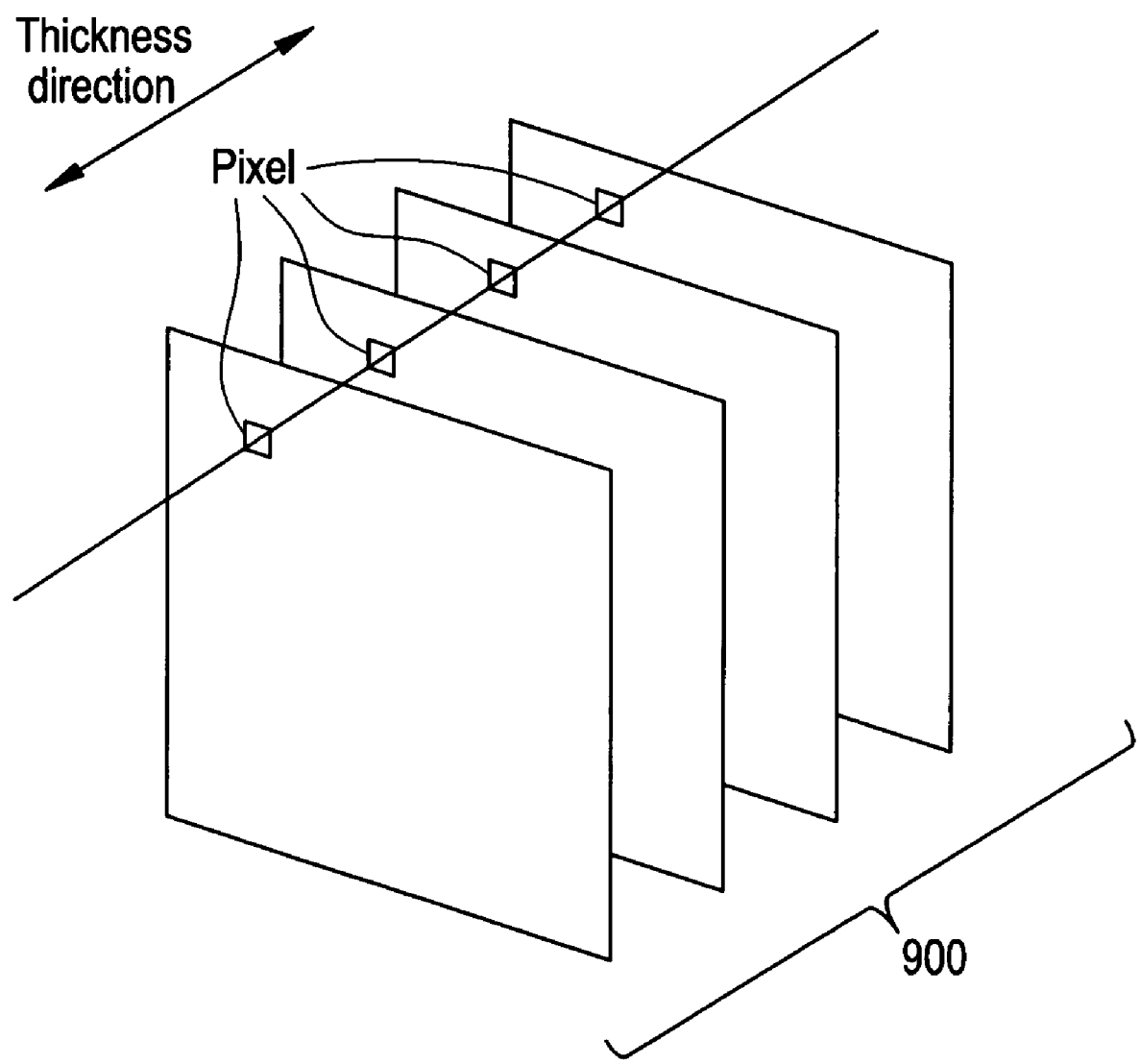
FIG. 14 is an explanatory diagram concerning production of a projection image in the second embodiment.

Next, the field change process image display of step S1002 will be described in conjunction with FIG. 11. FIG. 11 is a flowchart describing actions to be performed during field change process image display. First, the control unit 908 instructs the projection image data production means 910 to produce the projection image data 912 from the image data 900 produced at step S1001 (step S1101). FIG. 14 is an explanatory diagram illustratively showing an example of production of the projection image data 912. Herein, the image data 912 comprises a plurality of image data items produced by sweeping the probe 101 over a subject in a thickness direction with the irradiating direction, in which ultrasonic waves are irradiated, fixed. The pixel values located at the same pixel location in the image data items are added up, whereby a pixel value at the same pixel location in projection image data is produced.

Figure 15:
FIG. 15 is an explanatory diagram showing an example of the projection image produced in the second embodiment.

FIG. 15 shows an example of an image represented by the projection image data 912 produced from the image data 900 representing the images shown in FIG. 13. The images of fields fractionally showing blood flow are synthesized into one image. The image represented by the projection image data 912 shows all the fields in a region in which blood flow is present during the time elapsing from the instant blood or the like flows into the three-dimensional region of imaging to the instant the blood flows out of the three-dimensional region of imaging.

Thereafter, the control unit 908 instructs the field change process image data production means 920 to produce the field change process image data 924 (step 1102). Herein, the control unit 908 uses any of the time-phase image production means 921, maximum pixel value time image production means 922, and pixel value rise start time image production means 923 to produce the field change process image data 924 according to information on an instruction entered at the input unit 107. Incidentally, if the time-phase image production means 921 is selected, the images represented by the image data 900 as shown in FIG. 13 are time-phase images showing a time-sequential change in blood flow. The image data 900 is therefore adopted as the field change process image data 924 as it is.

Thereafter, based on information on an instruction entered at the input unit 107, the control unit 908 determines if the images represented by the field change process image data 924 are each superimposed on a background image that is the image represented by the projection image data 912 (step S1103). If the superimposition is not performed (determination is made in the negative at step S1103), the synthesis/output means 230 sequentially displays the images represented by the field change process image data 924 on the display unit 106 (step S1104).

Figure 16:
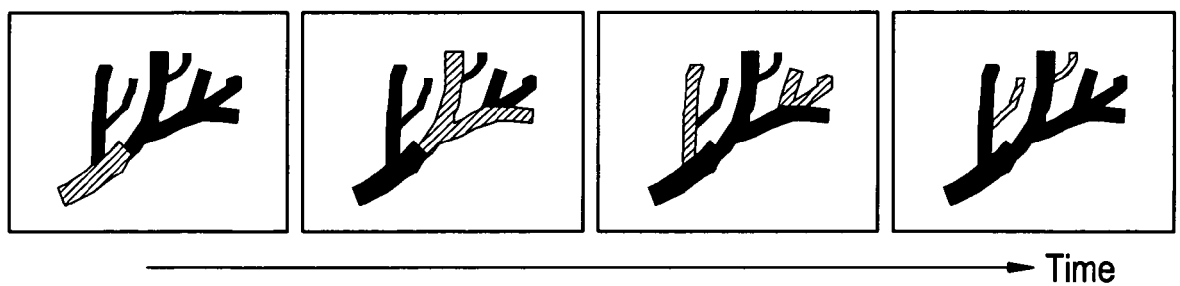
FIG. 16 is an explanatory diagram showing an example of images which are represented by field change process image data and on which the projection image produced in the second embodiment is superimposed.

Moreover, if the superimposition is performed (determination is made in the affirmative at step S1103), the control unit 908 instructs the synthesis/output means 230 to time-sequentially display on the display unit 106 the images represented by the field change process image data 924 by superimposing each of the images on the background image, that is, the image represented by the projection image data 912 (step S1105). FIG. 16 shows along an axis of abscissas serving as a time base the time-sequential change of the images, which are represented by the field change process image data 924 and superimposed on the background image represented by the projection image data 912, that is, a change in a region of imaging occurring in a thickness direction. In the case of FIG. 16, the field change process image data 924 is produced using the time-phase image production means 924 shown in FIG. 13.

Referring to FIG. 16, the image represented by the projection image data 912 as shown in FIG. 15 is contained as the background image in all the time-phase images. The time-phase images represented by the field change process image data 924 as shown in FIG. 13 are superimposed on the background image and displayed as hatched image portions. In FIG. 16, the images represented by the field change process image data 924 are the hatched image portions. Alternatively, the images represented by the field change process image data 924 may be displayed on the display unit 106 in a different color, for example, red.

As mentioned above, according to the second embodiment, the projection image data production means 910 uses the image data 900, which represents an image of a subject's region in which blood flow or the like is present, to produce the projection image data 912 representing a projection image composed of images of all fields in the region in which blood flow is present. The field change process image data production means 920 produces the field change process image data 924 that represents the images of the fields showing a process that the blood flow changes from field to field in the region of imaging. The synthesis/output means 230 superimposes each of the images represented by the field change process image data 924 on the image represented by the projection image data 912, and sequentially transmits the resultant image to the display means 109. Consequently, the process that the fields within the region in which blood flow is present change can be recognized in comparison with the image of the entire region including all the fields in which the blood flow is present.

According to the second embodiment, the probe 101 is manually swept over a subject. Alternatively, the probe 101 may be automatically swept over a subject using a machine. A probe having piezoelectric elements arranged in a two-dimensional array or a matrix may be used and electrically swept over a subject.

According to the second embodiment, a CFM-mode image, that is, an image produced by performing CFM is employed. Alternatively, a Doppler-mode image, a B-mode image, a B flow-mode image, or the like may be adopted.

Third Embodiment

The aforesaid first and second embodiments employ image data indicating a process that a contrast medium injected into a subject is infiltrated into the same region of imaging in a subject, or image data produced according to a CFM technique or the like so as to represent successive fields in a region over which the probe 101 is manually swept in a thickness direction substantially orthogonal to imaging sections. Each of the images represented by the image data is clearly grasped using an image, which is represented by image data produced by adding up a plurality of image data items, as a background image. As a similar constituent feature encompassing the foregoing ones, a plurality of image data items produced successively with the passage of time may be added up in order to produce continuous time field image data, and an individual image represented by image data may be displayed using an image represented by the continuous time field image data as a background image. The third embodiment is concerned with a case where an individual image represented by image data is clearly grasped using the image represented by the continuous time field image as a background image.

Figure 17:
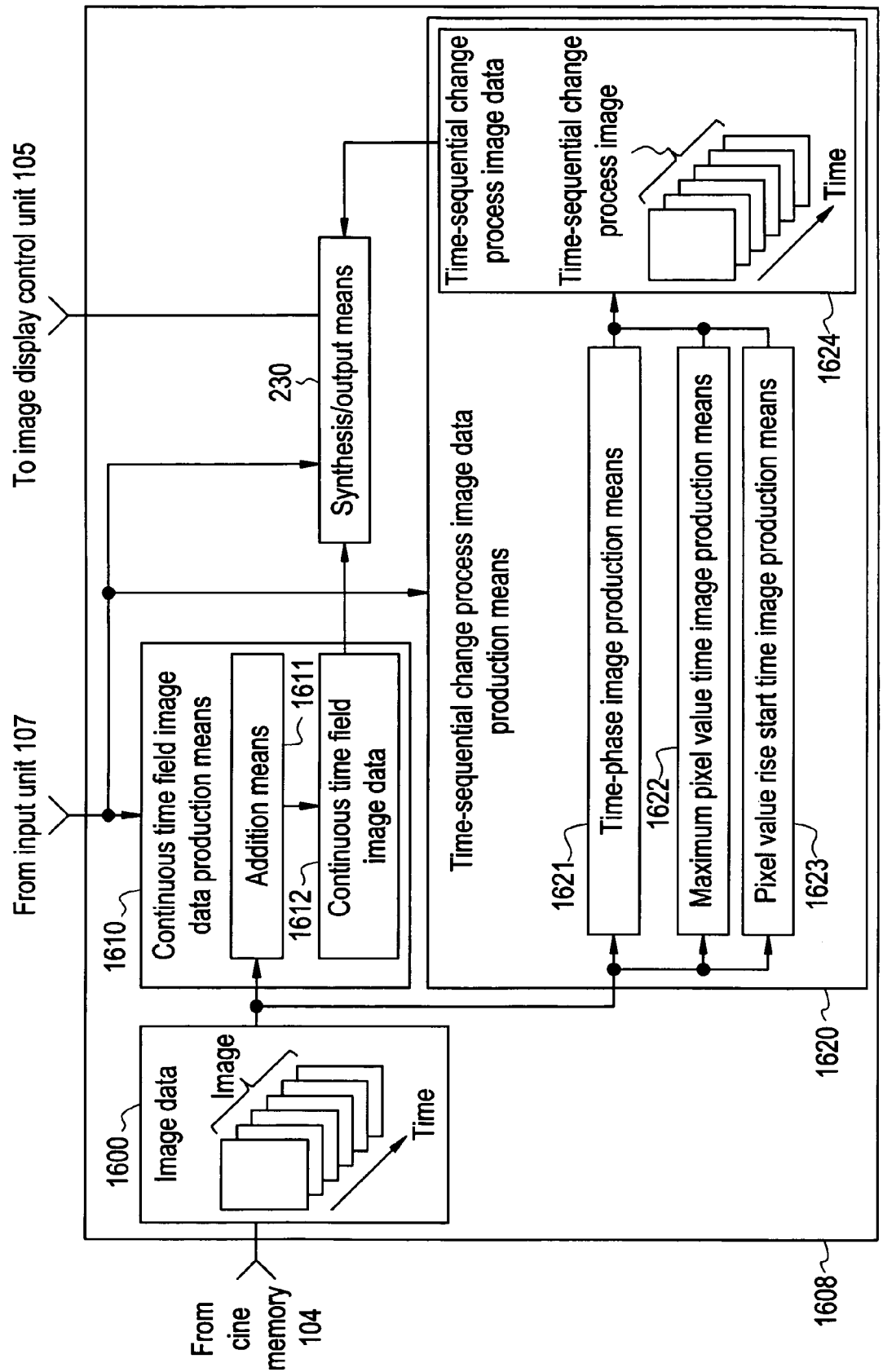
FIG. 17 is a functional block diagram showing the functional configuration of a control unit included in the third embodiment.

The third embodiment of the present invention has the same hardware configuration as the first embodiment shown in FIG. 1 except the control unit 108. The description of components other than the control unit 108 will be omitted. FIG. 17 is a functional block diagram showing the functional components of a control unit 1608 included in the third embodiment. The control unit 1608 is equivalent to the control unit 108 shown in FIG. 1.

The control unit 1608 comprises image data 1600, a continuous time field image data production means 1610, a time-sequential change process image data production means 1620, and a synthesis/output means 230. The image data 1600 is received from the cine memory 104 and composed of a plurality of time-sequential image data items produced by the probe 101.

The continuous time field image data production means 1610 includes an addition means 1611 for adding up pixel values located at the same pixel location in the plurality of image data items so as to produce image data representing one image. The continuous time field image data production means 1610 uses the addition means 1611 to produce continuous time field image data 1612, which represents one image, by adding up all the image data items constituting the image data 1600.

The time-sequential change process image data production means 1620 includes a time-phase image production means 1621, a maximum pixel value time image production means 1622, and a pixel value rise start time image production means 1623. The time-sequential change process image data production means 1620 uses the image production means to produce time-sequential change process image data 1624, which indicates the process that images are time-sequentially changed, from the image data 1600. Incidentally, the time-phase image production means 1621, maximum pixel value time image production means 1622, and pixel value rise start time image production means 1623 are identical to the time-phase image production means 221, maximum pixel value time image production means 222, and pixel value rise start time image production means 223 which are shown in FIG. 2. The description of the time-phase image production means 1621, maximum pixel value time image production means 1622, and pixel value rise start time image production means 1623 will therefore be omitted.

The synthesis/output means 230 superimposes an image represented by the continuous time field image data 1612 as a background image on each of images represented by the time-sequential change process image data 1624. The resultant image is sequentially displayed on the display unit 106 along a time base used as an index for the images represented by the time-sequential change process image data 1624. At this time, the image represented by the continuous time field image data 1612 and the images represented by the time-sequential change process image data 1624 which are superimposed on each other are colored to be visually discriminated from each other. For example, the image represented by the continuous time field image data 1612 is displayed as a monochrome image, and the images represented by the time-sequential change process image data 1624 are displayed as a color image of red or blue. The superimposition may be achieved using the image display control unit 105 so that the images to be superimposed on each other will be displayed at the same position on the display unit 106 or an image will be separately produced by superimposing images represented by different image data items on each other and then displayed on the display unit 106. The formula expressing the superimposition is identical to the formula (1).

Actions to be performed by the control unit 1608 are identical to those of the control unit 108 or 908 included in the first or second embodiment. The description of the actions will therefore be omitted.

As described above, according to the third embodiment, the continuous time field image data production means 1610 uses the image data 1600, which comprises a plurality of successive frame image data items acquired during a scan time, to produce the continuous time field image data 1612 by adding up the plurality of successive frame image data items acquired during the scan time. The time-sequential change process image data production means 1620 produces the time-sequential change process image data 1624 representing a plurality of frame images to be changed time-sequentially. The synthesis/output means 230 superimposes the image represented by the continuous time field image data on each of the images represented by the time-sequential change process image data, and sequentially transmits the resultant image to the display means 109. Consequently, a process that images represented by image data items are changed time-sequentially can be discerned in comparison with an image produced based on all the successive image data items acquired during the scan time.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasonic imaging apparatus comprising:
   an image data production device for producing image data comprising a plurality of frame image data items, the plurality of frame image data items representing a time-sequential change in a visualized region, after a contrast medium is injected into a subject;
   a display device for displaying images represented by the image data;
   a storage device for preserving the image data;
   an infiltrated field image data production device for producing infiltrated field image data using the image data, the infiltrated field image data representing a background image that renders all fields within the visualization region into which the contrast medium is infiltrated;
   an infiltration process image data production device for producing infiltration process image data using the image data, the infiltration process image data representing a plurality of image frames showing a process of infiltration of the contrast medium into the visualized region; and
   a synthesis/output device for one of superimposing and synthesizing each frame image of the plurality of frame images on or with the background image to generate a resultant image, and transferring the resultant image to the display device while sequentially changing the frame images according to the process.

2. The ultrasonic imaging apparatus according to claim 1, wherein the infiltrated field image data production device comprises an addition device for summating the image data representing the plurality of image frames.

3. The ultrasonic imaging apparatus according to claim 1, wherein the infiltrated field image data production device and infiltration process image data production device each comprises a subtraction device for subtracting reference image information that is devoid of information regarding the contrast medium from the image data.

4. The ultrasonic imaging apparatus according to claim 1, wherein the infiltration process image data comprises, as pixel information, pixel values included in the image data and that reflect amounts of the contrast medium.

5. The ultrasonic imaging apparatus according to claim 1, wherein the infiltration process image data comprises, as pixel information, times at which respective pixel values included in the image data acquire a maximum value.

6. The ultrasonic imaging apparatus according to claim 1, wherein the infiltration process image data comprises, as pixel information, time instants at which pixel values included in the image data start growing.

7. The ultrasonic imaging apparatus according to claim 1, further comprising an input unit that, when the image data is three-dimensional image data, is used to enter a position of a section image, the entered position is transmitted to the infiltrated field image data production device, infiltration process image data production device, and synthesis/output device.

8. The ultrasonic imaging apparatus according to claim 7, wherein the synthesis/output device sequentially changes a position of the section image based on the transmitted position, according to the process.

9. The ultrasonic imaging apparatus according to claim 8, wherein the sequential change is achieved by rotating the section image.

10. The ultrasonic imaging apparatus according to claim 7, wherein the synthesis/output device comprises a production device for producing two-dimensional image information regarding the section image using projection information produced from the infiltrated field image data and the infiltration process image data.

11. The ultrasonic imaging apparatus according to claim 10, wherein the projection information represents sum totals of projection values, the sum totals produced from the infiltrated field image data and the infiltration process image data and calculated in a direction orthogonal to the section image.

12. An image processing apparatus comprising:
an interface via which pieces of tomographic image information are received, the pieces of tomographic image information representing a time-sequential change in a visualized region, after a contrast medium is injected into a subject;
a display device for displaying images represented by the pieces of tomographic image information;
a storage device for preserving the pieces of tomographic image information;
an infiltrated field image data production device for producing infiltrated field image data using the pieces of tomographic image information, the infiltrated field image data representing a background image that renders all fields in the visualized region into which the contrast medium is infiltrated, the fields rendered in respective tomographic images;
an infiltration process image data production device for producing infiltration process image data using the pieces of tomographic image information, the infiltration process image data representing a plurality of image frames showing a process of infiltration of the contrast medium into the visualized region; and
a synthesis/output device for one of superimposing and synthesizing each frame image of the plurality of frame images on or with the background image to generate a resultant image, and transmitting the resultant image to the display device while sequentially changing the frame images according to the process.

13. The image processing apparatus according to claim 12, wherein the pieces of tomographic image information comprise image information acquired by an ultrasonic imaging apparatus.

14. The image processing apparatus according to claim 12, wherein the infiltrated field image data production device comprises an addition device for summating the pieces of tomographic image information.

15. The image processing apparatus according to claim 12, wherein the infiltration process image data comprises, as pixel information, pixel values that are included in the pieces of image information and that reflect amounts of the contrast medium.

16. The image processing apparatus according to claim 12, wherein the synthesis/output device displays each frame image of the plurality of frame images superimposed on the background image in a color different from a color in which the background image is displayed.

* * * * *